US00PP20409P2

(12) United States Plant Patent
Sidhu

(10) Patent No.: US PP20,409 P2
(45) Date of Patent: Oct. 13, 2009

(54) ***VINCA MINOR* PLANT NAMED 'VINSID 1'**

(50) Latin Name: *Vinca minor*
Varietal Denomination: Vinsid 1

(76) Inventor: Gurjit Sidhu, Sidhu & Sons Nursery Ltd. 9623 Sylvester Rd., Mission, BC V2V7K6 (CA)

( * ) Notice: Subject to any disclaimer, the term of this patent is extended or adjusted under 35 U.S.C. 154(b) by 0 days.

(21) Appl. No.: 12/229,575

(22) Filed: Aug. 25, 2008

(51) Int. Cl.
*A01H 5/00* (2006.01)

(52) U.S. Cl. ..... Plt./226

(58) Field of Classification Search ..... Plt./263, Plt./263.1, 226
See application file for complete search history.

*Primary Examiner*—Susan B McCormick Ewoldt
(74) *Attorney, Agent, or Firm*—Penny J. Aguirre

(57) ABSTRACT

A new cultivar of *Vinca minor* named 'Vinsid 1' that is characterized by its variegated foliage with leaves that emerge having yellow-green centers with darker green margins and mature to leaves with darker green centers and very dark green margins and by its large purple-blue flowers that are present in mid spring and then sporadically throughout the summer.

1 Drawing Sheet

Botanical classification: *Vinca minor.*
Cultivar designation: 'Vinsid 1'.

BACKGROUND OF THE INVENTION

The present invention relates to a new and distinct cultivar of *Vinca minor* and will be referred to hereafter by its cultivar name, 'Vinsid 1'. 'Vinsid 1' is an evergreen vine used in the landscape as a groundcover.

The inventor discovered 'Vinsid 1' as a naturally occurring branch mutation of *Vinca Minor* 'Mrs. Bowles' (not patented) in a container at his nursery in April 2005 in Mission, British Columbia, Canada.

Asexual reproduction of the new cultivar was first accomplished by stem cuttings in Mission, British Columbia, Canada in winter of 2005 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Vinsid 1' as unique from all other selections and forms of *Vinca minor* known to the inventor.

1. 'Vinsid 1' exhibits variegated foliage that has new growth in which the leaf centers are yellow-green with darker green margins. As the leafs mature, the centers become less distinct and darker green with the margins a blend of darker green and black.
2. 'Vinsid 1' exhibits large purple-blue flowers in mid spring and then sporadically throughout the summer.

'Vinsid 1' differs from its parent plant, 'Mrs. Bowles', in that 'Mrs. Bowles' has smaller flowers and foliage that is not variegated. 'Vinsid 1' can be compared to other cultivars of *Vinca minor* with yellow and green variegated foliage. 'Aureovariegata' (not patented), differs in having centers that are green and turn shades of golden green as they mature with thin white margins. 'Illumination' (U.S. Plant Pat. No. 12,132) is similar in having yellow-green centers and dark green margins, however the centers become creamy yellow as the leaves mature, whereas 'Vinsid 1' has leaf centers become darker green as the leaves mature.

BRIEF DESCRIPTION OF THE DRAWING

The accompanying photograph depicts plant parts taken from a two-year-old plant of 'Vinsid 1' as grown in a 2 qt. container in Mission, British Columbia, Canada. The plant was grown outdoors in bright shade. In the Photograph, the newly emerging foliage is shown on the bottom right, mature foliage is shown on the left, and the flowers are shown on the top right. The colors in the photograph are as close as possible with the digital photography and printing techniques utilized and the color descriptors in the Detailed Botanical Data most accurately describes the new *Vinca minor.*

BOTANICAL DESCRIPTION OF THE PLANT

The following is a detailed description of 2-year old plants of the new cultivar as grown outdoors in 2 qt containers in Mission, British Columbia, Canada. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—About 3 weeks in late spring and then sporadically throughout the summer.

*Plant habit.*—Herbaceous perennial, rhizomatous, clump-forming but slowly spreading as a groundcover, growth habit is initially upright then prostrate as the branches vine,

*Height and spread.*—About 18 cm in height with lateral vines reaching about 100 cm in spread (2 year-old plant).

*Hardiness.*—At least to U.S.D.A. Zone 4.

*Diseases and pests.*—No susceptibility or resistance to diseases or pests has been observed.

*Root description.*—Fleshy roots arising from knotty rhizomes.

Growth and propagation:

*Propagation.*—Stem cuttings.

*Growth rate.*—Vigorous.

Stem description:

*Shape.*—Round, solid.

*Stem color.*—New growth; 150C, maturing stems; 174B to 174C.

*Stem size.*—An average of 1.8 mm in diameter, indeterminate in length.

*Stem surface.*—Glabrous.

*Branching.*—Most typically arise from base with occasional secondary branching, average of 18 basal branches in a 2 qt container by late summer, continuously produced.

Foliage description:

*Leaf shape.*—Elliptic to ovate.

*Leaf division.*—Simple.

*Leaf base.*—Cuneate.

*Leaf apex.*—Acute.

*Leaf venation.*—Pinnate, 144B to 144C on upper surface, 144D on lower surface.

*Leaf margins.*—Entire.

*Leaf attachment.*—Petiolate.

*Leaf arrangement.*—Opposite.

*Leaf size.*—Average of 2.7 in length and 1.6 cm in width.

*Leaf surface.*—Upper surface; glabrous and satiny to shiny, lower surface; glabrous and dull to satiny.

*Internode length.*—Average of 2 cm.

*Leaf variegation pattern.*—New leaves; centers are yellow green with darker green margins with pattern irregular in shape with the center color comprising about 75% of the leaf area, mature leaves; centers become less distinct and darker green with the margins a blend of darker green and black, lower surfaces have narrower margins with the centers comprising about 90% of the leaf area.

*Leaf color.*—New leaves upper surface; centers 144B to 144D with margins 137B, new leaves upper surface; centers 145A to 145B, mature leaves upper surface; 147A with margins a blend of 147A and 202A, mature leaves lower surface; centers a blend of 146A to 146C with margins 147A.

*Leaf quantity.*—Average of 9 pairs on a stem 20 cm in length.

*Petioles.*—Average of 6 mm in length and 1.5 mm in width, curved upward from stem, glabrous surface, 145A in color.

Flower description:

*Inflorescence type.*—Solitary, salviform, emerge from axillary nodes.

*Lastingness of flowers.*—About 4 days.

*Flower fragrance.*—None.

*Flower size.*—About 1.2 cm in depth, about 2.9 cm in width, comprised of a narrow tube 3 mm in length and width at base with campanulate tube about 6 mm in length and 5 mm in width, the center of the tube is 5 mm in diameter.

*Flower number.*—2 to 3 per leaf node in spring.

*Flower buds.*—Kidney-shaped, about 2 cm in length and 5 mm in width, 92B to 92C in color with calyx portion 144A.

*Sepals.*—5, un-fused, about 3 mm in length and 2 mm in width, 144A to 144B in color on upper and lower surface, truncate base, acute apex, surface is glabrous on both surfaces, forms a calyx with an open campanulate form about 3 mm in length and 5 mm in width, persistent.

*Petals size.*—5, base fused into tube about 1 cm in length and 5 mm in width with spreading free portion about 1.2 cm in length and 7 mm in width, rounded apex, entire margin, color of upper surface; blend of 92A and 92B with center of tube NN155A with vertical markings of 92B to 92C about 3 mm in length and 2 mm in width, color of lower surface; blend of 92B and 92C, with very base of tube 150D.

*Peduncle.*—Oval, about 1 cm in length, about 1.5 mm in width, 144D in color, glabrous surface.

Reproductive organs:

*Gynoecium.*—1 Pistil, 6 mm in length and 2 mm in width, style; 4 mm in length, 0.8 mm in width 145D in color with membranous ring at apex 1 mm in diameter and 0.5 mm in length and 138B in color, stigma is a plumose mound about 1 mm in depth and 1.5 mm in diameter and NN155A in color, ovary is superior, 4-locular, globose in shape, about 1 mm in length and diameter and 144A in color.

*Androcoecium.*—5 stamens. styles are adnate to corolla tube, about 5 mm in length, translucent and 145D in color, anthers basifixed, about 2 mm in length and 1 mm in, width, villose, and 163C in color, pollen is moderate in quantity and 155A in color.

*Fruit/seed.*—Not observed, the small, cylindrical fruit follicles of *Vinca minor* are very rarely ever observed in cultivation.

It is claimed:

1. A new and distinct cultivar of *Vinca minor* plant named 'Vinsid 1' as herein illustrated and described.

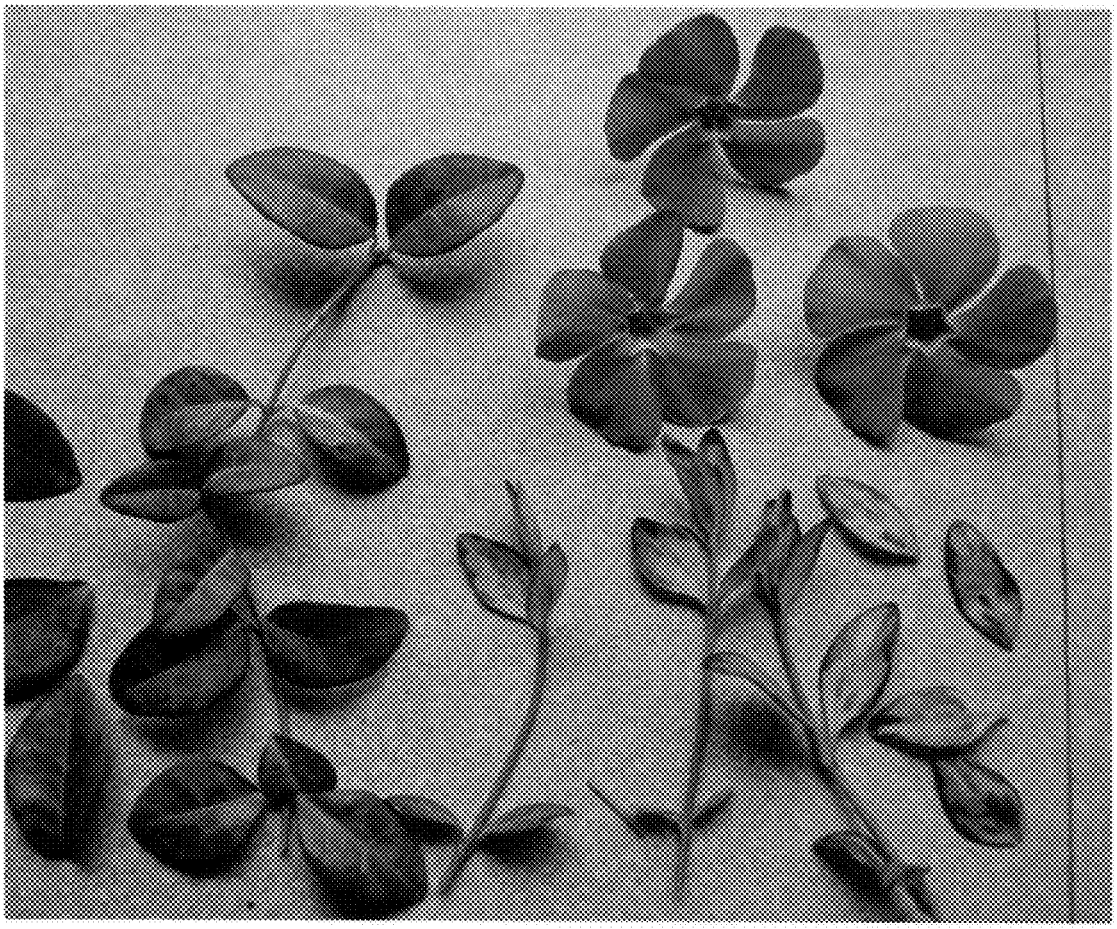

* * * * *